United States Patent [19]

Bremer

[11] Patent Number: 5,122,132

[45] Date of Patent: Jun. 16, 1992

[54] SKULL PIN WITH ENHANCED SHEAR RESISTANCE

[75] Inventor: Paul W. Bremer, Jacksonville, Fla.

[73] Assignee: Bremer Medical, Inc., Jacksonville, Fla.

[21] Appl. No.: 739,336

[22] Filed: Aug. 1, 1991

[51] Int. Cl.⁵ .................. A61B 17/56; F16B 25/00
[52] U.S. Cl. ........................ 606/72; 411/386; 606/76
[58] Field of Search ............ 606/54, 72, 73, 65, 606/130, 61, 75; 411/386; 128/69

[56] References Cited

U.S. PATENT DOCUMENTS

| | | | |
|---|---|---|---|
| 2,532,296 | 12/1950 | Giesen | 606/73 |
| 3,053,256 | 9/1962 | Cooper | 606/130 |
| 3,223,087 | 12/1965 | Vladyka | 606/130 |
| 3,790,507 | 2/1974 | Hodosh | 606/72 |
| 4,463,753 | 8/1984 | Gustilo | 606/73 |
| 4,475,550 | 10/1984 | Bremer et al. | 606/165 |
| 4,612,930 | 9/1986 | Bremer | 606/130 |
| 4,706,665 | 11/1987 | Gouda | 606/130 |
| 4,793,335 | 12/1988 | Frey | 606/73 |
| 4,838,264 | 6/1989 | Bremer | 606/72 |
| 5,030,220 | 7/1991 | Howland | 606/73 |

OTHER PUBLICATIONS

S. Garfin et al. "Structural Behavior of the Halo Orthosis Pin-Bone Interface: Biomechanical Evaluation of Standard and Newly Designed Stainless Steel Halo Fixation Pins", SPINE, vol. 11, No. 10, 1986, pp. 977-981.

Bremer Medical Brochures "Halo Accessories", Adjustable Ring Traction Sets, and Halo Crown ®; 1987, 1990.

Primary Examiner—Robert A. Hafer
Assistant Examiner—Michael Brown
Attorney, Agent, or Firm—Nixon & Vanderhye

[57] ABSTRACT

A skull pin provides greater resistance to shear forces so that it may be more readily made of titanium, ceramic or gem stone, yet still prevents undue penetration, and can be tightened if wear or erosion of the skull results from cyclic loading. The pin is used with a halo or cervical traction ring, and has a main, externally threaded, circular cylindrical body, and a skull engaging portion. The skull engaging portions is formed by first and second concentric, in-line cylinders terminating in conical sections, the first conical section terminating in the second cylinder (which resists shear forces much better than conventional skull pins), and the second conical section terminating in a pointed tip. The first cylinder has a diameter of about 0.18 inches, the first conical section has a length of about 0.09 inches and approximately a 60° taper angle, the second cylinder has a length of about 0.03 inches and a diameter of about 0.07 inches, and the second conical section has approximately a 60° taper angle.

20 Claims, 1 Drawing Sheet

SKULL PIN WITH ENHANCED SHEAR RESISTANCE

BACKGROUND OF THE INVENTION

In many medical and operative procedures, it is necessary to hold a patient's head in a particular position. For example, a patient's head is held stationary while a fracture or dislocation of the cervical spine is healing. Typical structures for performing that function are conventional halos, and cervical traction rings, such as shown in U.S. Pat. Nos. 4,475,550 and 4,612,930, the disclosures of which are hereby incorporated by reference herein.

Conventional skull pins which are utilized with halos and cervical traction rings sometimes do not hold in the skull bone as securely as desired. There is sometimes a tendency for the pins to pull out when subjected to sideways (e.g. shear) forces. Therefore it is desirable to provide a more secure fixation for skull pins than has traditionally been provided.

Conventional skull pins also are typically made of medical grade stainless steel. Such pins have the drawback, however, of artifacting much more than bone when subjected to an imaging procedure. If the pins are made of titanium, which does not artifact nearly as much as stainless steel, then the tips have a tendency to break off as a result of shear forces. If this skull engaging portions of the pins are made out of biologically compatible ceramic material, such as shown in said U.S. Pat. No. 4,612,930, again there is the possibility that the tips will break off since the material is relatively brittle.

There have been experimental pins tested, such as described in a 1986 article in *Spine Medical Journal*, at pages 977 through 981, which seek to improve halo skull pin design by making the fixation more secure (providing shear resistance), while enhancing penetration prevention. Such experimental pins, however, are not practical since under cyclical loading the skull bone will wear or erode, and such experimental pins are not capable of being advanced so as to always be properly engaging the bone to accommodate wear or erosion.

According to the present invention, a skull pin is provided which is an improvement over both conventional skull pins— having enhanced shear resistance, and fixation to the skull and allowing them to be made of a wider variety of materials— and the experimental pins discussed above, and capable of being retightened if the skull bone is subjected to wear or erosion.

The skull pin according to the present invention has a design which allows the tip thereof to hold more securely in the skull when subjected to sideways forces, and to be made out of a more brittle material than has been practically utilized in the past, typically a material that does not significantly artifact, such as titanium, or a material that does not artifact significantly more than bone, such as biologically compatible ceramic (single crystal alumina ceramic), or a gem stone (e.g., sapphire).

According to one aspect of the present invention, a skull pin is provided having a main cylindrical body portion, and a skull engaging portion. The skull engaging portion comprises first and second concentric, in-line cylinders terminating in conical sections, the first conical section terminating in the second cylinder, and the second conical section terminating in a pointed tip. While the dimensions may vary for a number of reasons, it is preferred that the cylinders be circular in cross section, with the first cylinder having a diameter of about 0.18 in.; the first conical section a length of about 0.09 in. and approximately a 60° taper; the second cylinder having a length of about 0.03 in. (e.g., about 1/32 of an inch) and a diameter of about 0.07 in.; and the second conical section having approximately a 60° taper. The skull pin, particularly, the skull engaging tip portion thereof, may be made from medical grade stainless steel, but preferably is made of titanium, biologically compatible ceramic, a gem stone, or a like material that does not significantly artifact. The skull pin is typically used in combination with a halo or cervical traction ring, as is conventional.

According to another aspect of the present invention, a skull pin is provided having a skull engaging portion thereof made of material which does not artifact significantly. The skull engaging portion is a pointed tip termination, a sideways (shear) force resisting, fixation enhancing section (e.g., a short cylindrical section having a length approximately equal to or slightly less than the thickness of the outer table of a human skull) adjacent the pointed tip to minimize the probability that the tip will be snapped off, and a conical section for facilitating tight adjustment of the pin to a human skull if the skull wears or erodes as a result of cyclical loading.

According to another aspect of the present invention, a skull pin is provided comprising: A main substantially cylindrical body elongated in a dimension of elongation, and having first and second ends. A skull engaging portion connected to the main body and extending outwardly from the first end thereof in the dimension of elongation. A stepped tip portion of the skull engaging portion, the stepped tip portion remote from the main body, and having: a first conical section closest to the cylinder first end, the first conical section having a diameter tapering from its largest extent to its smallest extent moving away from said main body in said dimension of elongation, and at its largest area less than the largest cross-sectional dimension of the main cylindrical body; the first conical section terminating in a short cylindrical section extending outwardly from the first conical section in the dimension of elongation, the short cylindrical section having a largest cross-sectional dimension which is much smaller than the largest cross-sectional dimension of the main body; and the short cylindrical section terminating at an end thereof most remote from the main body in a second conical section, which itself terminates in a pointed tip at an end thereof most remote from the main body. The main body is circular in cross section and exteriorly threaded.

It is a primary object of the present invention to provide an improved skull pin, capable of better resisting shear forces, enhancing fixation, while still facilitating tight adjustment in a skull even if the skull wears or erodes as a result of cyclical loading, and allowing a wide variety of different materials to be used in construction, which materials may be chosen so that they do not significantly artifact. This and other objects of the invention will become clear from an inspection of the detailed description of the invention, and from the appended claims.

DETAILED DESCRIPTION OF THE DRAWINGS

Figure 1:
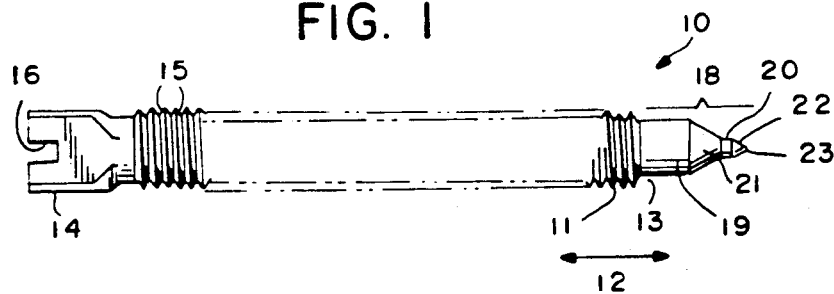
FIG. 1 is a side view of an enlargement of an exemplary skull pin according to the present invention.
Figure 2:
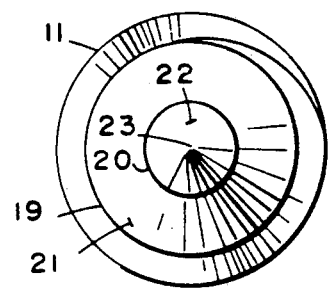
FIG. 2 is an end view, looking in at the point, of the skull pin of FIG. 1.

An exemplary skull pin according to the present invention is shown generally by reference numeral 10 in FIGS. 1 and 2. The pin comprises a main, substantially cylindrical (preferably circular in cross section) body 11 elongated in a dimension of elongation 12 and having first and second ends 13, 14. Preferably the body 11 has exterior screw threads 15 formed thereon. At the second end 14, there preferably is provided some mechanism for facilitating adjustment of the pin 10 position with respect to a patient's head, such as means defining a slot 16 for receipt of a screwdriver blade.

Figure 3:
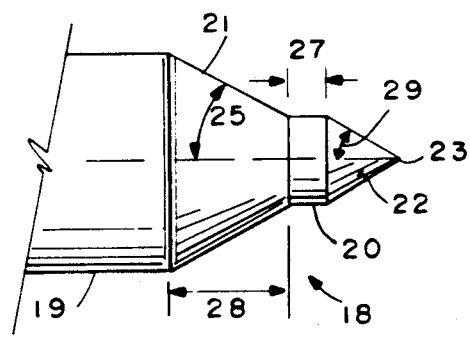
FIG. 3 is a detail, greatly enlarged, schematic side view of the pointed tip portion of the pin of FIG. 1.

The pin 10 also includes a skull engaging portion, shown generally by reference numeral 18, connected to the main body 11, and extending outwardly from the first end 13 thereof in the dimension of elongation 12. The skull engaging portion 18 includes the stepped tip portion, which — as illustrated most clearly in FIGS. 1 and 3— comprises first and second concentric in-line cylinders 19, 20 terminating in conical sections, the first conical section 21 terminating in the second cylinder 20, and the second conical section 22 terminating in a pointed tip 23. The first cylinder 19 and first conical section 21 are closest to the body 11 and extend outwardly in the dimension of elongation 12 therefrom, and the largest diameter of the first conical section 21 is less than the outside diameter of the body 11. The short, second cylindrical section 20 has a diameter which is much smaller than the diameter of the main body 11.

The taper of the first conical section 21 is preferably about the same as the taper of conventional skull pins used by Bremer Medical, Inc. That is, the taper angle 25 is about 60°. The first conical section 21 allows the pin 10 to be advanced to accommodate erosion or wear of the skull bone as a result of cyclical loading.

The second cylindrical section 20 has a length 27 which is approximately equal to, or slightly less than, the thickness of the outer table of a normal human skull, e.g., about 1/32 of an inch, or about 0.3 (e.g., 0.313) inches. This distance is enough to perform its designed function of enhancing the shear force resistance (i.e. providing better fixation to the skull), which was an object of the experimental pins in the "SPINE" journal article cited above.

While there may be some deviation of the dimensions of the elements of the skull engaging tip portion 18, it is preferred that the diameter of the first cylindrical section 19 be about 0.18 inches, the diameter of the second cylindrical section 20 be about 0.07 inches (e.g., about 0.0722 in.), the length 28 of the first conical section 21 be about 0.09 inches (e.g., about 0.0934 in.), and the taper angle 29 of the conical section 22 be about 60°.

It is preferable that the skull pin 10, or at least the skull engaging portion 18 thereof, be of a material with minimal artifact capability. This enhances uses of the skull pins 10 during conventional imaging, as with a CT scanner. While the pin 10 may be made of medical grade stainless steel, it is preferable that it be made of titanium, or at least the skull engaging tip portion 18 be made of titanium, or biologically compatible ceramic material such as single crystal alumina ceramic (as disclosed in said U.S. Pat. No. 4,612,930), or of a gem stone (e.g., sapphire). In particular, single crystal alumina ceramic and sapphire do not artifact significantly more than bone. Despite the fact that titanium, ceramic and sapphire are brittle, there is much less tendency for the points of the pins 10 to break off than with conventional pins (in addition to providing better fixation) since the cylindrical section 20 provides enhanced resistance to shear forces.

Figure 4:
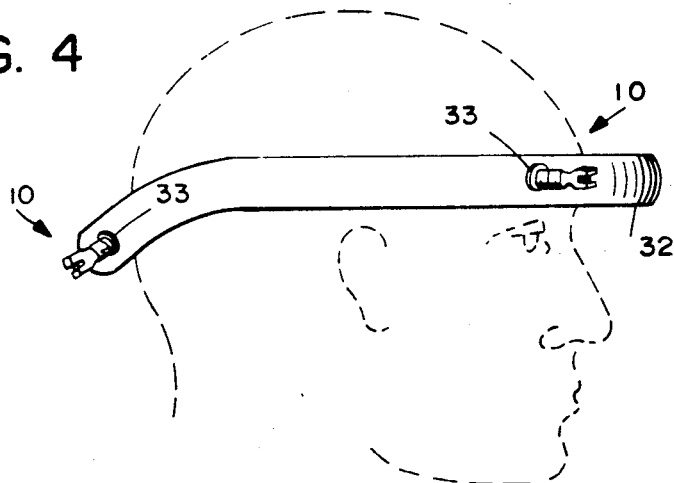
FIG. 4 is a side view of a pair of skull pins according to the invention shown in use with a cervical traction ring, and on a patient's head.

FIG. 4 illustrates a pair of skull pins 10 according to the invention (actually four will typically be used) in association with a cervical traction ring 32, such as shown in said U.S. Pat. No. 4,612,930. The pins 10 have the external threads 15 thereof threaded into engagement with internal threads of openings 33, so that the positions of the pins 10 with respect to the patient's head may be adjusted as desired during installation, and to accommodate wear or erosion.

Figure 5:
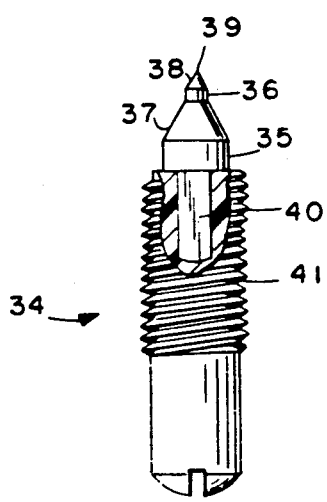
FIG. 5 is a side view, partly in cross section and partly in elevation, of a second embodiment of an exemplary skull pin according to the present invention.

FIG. 5 shows a skull pin 34 from said U.S. Pat. No. 4,612,930 that may be utilized in place of the pin 10, and is substantially identical to the skull pin illustrated in said U.S. Pat. No. 4,612,930 except that the tip is constructed according to the present invention, having first and second cylindrical portions 35, 36, first and second conical portions 36, 38, and the tip 39. Shaft 40 is connected to the skull engaging tip portion of the pin 34 and is embedded in the main cylindrical body 41, which is preferably a type of plastic such as described fully in said U.S. Pat. No. 4,612,930.

It will thus be seen that according to the present invention an improved skull pin, particularly for use with halos and cervical traction rings, is provided. While the invention has been herein shown and described in what is presently conceived to be the most practical and preferred embodiment, it will be apparent to those of ordinary skill in the art that many modifications may be made thereof within the scope of the invention, which scope is to be accorded the broadest interpretation of the appended claims so as to encompass all equivalent structures and devices.

What is claimed is:

1. A skull pin comprising:

a main, substantially cylindrical body elongated in a dimension of elongation, and having first and second ends;

a skull engaging portion connected to said main body and extending outwardly from said first end thereof in said dimension of elongation; and a stepped tip portion of said skull engaging portion, said stepped tip portion remote from said main body, and having: a first smooth surfaced conical section closest to said main body first end, said first conical section having a diameter tapering from its largest extent to its smallest extent moving away from said main body in said dimension of elongation, and at its largest area less than the largest cross-sectional dimension of said main cylindrical body; said first conical section terminating in a short smooth surfaced cylindrical section extending outwardly from said first conical section in said dimension of elongation, said short cylindrical section having its largest cross-sectional dimension much smaller than the largest cross-sectional dimension of said main body; and said short cylindrical section terminating at an end thereof most remote from said main body in a second smooth surfaced conical section, which itself terminates in a pointed tip at an end thereof most remote from said main body.

2. A skull pin as recited in claim 1 wherein said main body is circular in cross section, and exteriorly threaded.

3. A skull pin as recited in claim 2 wherein said short cylindrical section is circular in cross section and has a diameter equal to the smallest diameter of said first conical section.

4. A skull pin as recited in claim 3 wherein said short cylindrical section has a length in said dimension of elongation approximately equal to or slightly less than the thickness of the outer table of a normal human skull.

5. A skull pin as recited in claim 4 wherein said length of said short cylindrical section is about 0.03 inches.

6. A skull pin as recited in claim 5 wherein said short cylindrical section is circular in cross-section and has a diameter of about 0.07 inches.

7. A skull pin as recited in claim 6 wherein each of said first and second conical sections has a taper angle of approximately 60°.

8. A skull pin as recited in claim 6 further comprising a circular in cross-section cylindrical portion between said cylindrical body and said first conical section, said cylindrical portion having a diameter of about 0.18 inches.

9. A skull pin as recited in claim 2 wherein at least said stepped tip portion is made from a material selected from the group consisting essentially of titanium, medical grade stainless steel, biologically compatible ceramic, and gem stone.

10. A skull pin as recited in claim 9 wherein said ceramic is single crystal alumina ceramic, and wherein said gem stone is sapphire.

11. A skull pin as recited in claim 2 further comprising means defining a slot at said second end of said main body for receipt of a screwdriver blade.

12. A skull pin having at least the skull engaging portion thereof made of a material which does not artifact significantly, said skull engaging portion having a pointed tip termination, a shear force resisting, fixation enhancing, section adjacent said pointed tip, and a smooth surface conical section for facilitating tight adjustment of said pin in a human skull if the skull wears or erodes as a result of cyclical loading.

13. A skull pin as recited in claim 12 wherein said shear force resisting, fixation enhancing, section is a short smooth surfaced cylindrical section having a length approximately equal to or slightly less than the thickness of the outer table of a human skull.

14. A skull pin as recited in claim 12 wherein said material is selected from the group consisting essentially of titanium, gem stone, and biologically compatible ceramic.

15. A skull pin as recited in claim 14 further comprising a main cylindrical body having a circular cross section that is externally threaded.

16. A skull pin as recited in claim 15 wherein said main body is of a different material than said skull engaging portion of said pin.

17. A skull pin as recited in claim 15 wherein said main body and said skull engaging portion are of titanium.

18. A skull pin as recited in claim 12 further comprising a main cylindrical body having a circular cross section that is externally threaded, and in combination with halo or cervical traction ring, said main body being received within an interiorly threaded opening in said halo or cervical traction ring.

19. A skull pin having a main cylindrical body portion, and a skull engaging portion, said skull engaging portion comprising first and second concentric, in-line cylinders terminating in smooth surfaced first and second conical sections, the first conical section terminating in the second cylinder, and the second conical section terminating in a pointed tip.

20. A skull pin as recited in claim 19 wherein said cylinders are circular in cross section, and wherein said first cylinder has a diameter of about 0.18 inches, said first conical section has a length of about 0.09 inches, and said second cylinder is smooth surfaced and has a length of about 0.03 inches and a diameter of about 0.07 inches.

* * * * *